United States Patent [19]

Litt et al.

[11] Patent Number: 5,077,400

[45] Date of Patent: Dec. 31, 1991

[54] DNA PROBE WHICH REVEALS A HYPERVARIABLE REGION ON HUMAN CHROMOSOME 17

[75] Inventors: Michael Litt, Portland; Sophia K. Kondoleon, Lake Oswego, both of Oreg.

[73] Assignee: State of Oregon ... Oregon Health Sciences University, Portland, Oreg.

[21] Appl. No.: 238,647

[22] Filed: Aug. 30, 1988

Related U.S. Application Data

[63] Continuation-in-part of Ser. No. 103,021, Sep. 30, 1987, Pat. No. 5,026,837, and a continuation-in-part of Ser. No. 54,760, May 27, 1987, Pat. No. 4,980,461, and a continuation-in-part of Ser. No. 53,320, May 22, 1987, and a continuation-in-part of Ser. No. 46,831, May 4, 1987, abandoned.

[51] Int. Cl.$^5$ .................. C07H 21/04; C12Q 1/68
[52] U.S. Cl. ............................ 536/27; 435/6; 435/91; 436/501; 935/77; 935/78
[58] Field of Search ............ 435/6, 91; 436/501; 536/27; 935/77, 78

[56] References Cited

U.S. PATENT DOCUMENTS

| | | | |
|---|---|---|---|
| 4,302,204 | 11/1981 | Wahl et al. | 23/230.3 |
| 4,358,535 | 11/1982 | Falkow et al. | 435/5 |
| 4,399,216 | 8/1983 | Axel et al. | 435/6 |
| 4,468,464 | 8/1984 | Cohen et al. | 435/317 |
| 4,594,318 | 6/1986 | Gusella et al. | 435/6 |
| 4,599,303 | 7/1986 | Yabusaki et al. | 435/6 |
| 4,623,619 | 11/1986 | Owerbach et al. | 435/6 |

OTHER PUBLICATIONS

Jeffreys et al., "Individual-Specific 'Fingerprints' of Human DNA", *Nature* 316:76-79 (1985).
Wyman and White, "A Highly Polymorphic Locus in Human DNA", *Proc. Natl. Acad. Sci. U.S.A.*, 77:6754-6758 (1980).
Nakamura et al., "Characterization of a Human 'Midisatellite' Sequence", *Nucl. Acids Res.* 15:2537-2547 (1987).
Buroker et al., "A Hypervariable DNA Region on Human Chromosome 1p", *Genetics* 113:Supplement No. 1, part 2, p. 564 (1986).
Litt et al., "A Highly Polymorphic Locus in Human DNA Revealed by Probes from Cosmid 1-5 Maps to Chromosome 2q35→37", *Am. J. Hum. Genet.* 38:288-296 (1986).
Litt and White, "A Highly Polymorphic Locus in Human DNA Revealed by Cosmid-Derived Probes", *Proc. Natl. Acad. Sci. U.S.A.*, 82:6206-6210 (1985).
Bufton et al., "Four Restriction Fragment Length Polymorphisms Revealed by Probes from a Single Cosmid Map to Chromosome 19", *Am. J. Hum. Genet.*, 38:447-460 (1986).
Buroker et al., "A Hypervariable Region at the D19S11 Locus", *Hum. Genet.*, 76:90-95 (1987).
Bufton et al., "A Highly Polymorphic Locus on Chromosome 16q Revealed by a Probe from a Chromosome-Specific Cosmid Library", *Hum. Genet.*, 74:425-431 (1986).

Primary Examiner—Robert A. Wax
Assistant Examiner—Ardin H. Marschel
Attorney, Agent, or Firm—Klarquist, Sparkman, Campbell, Leigh & Whinston

[57] ABSTRACT

A DNA probe p144-D6 is homologous to at least a portion of a hypervariable DNA region located on chromosome 17(17p13) in the human genome. The DNA region displays a restriction fragment length polymorphism when digested with certain restriction endonucleases. Unrelated invididuals often display unique fragment patterns on Southern blots probed with p144-D6. The probe can be used to produce a genetic "fingerprint" for establishing human identity, determining engraftment of bone marrow transplants, determining parentage, and otherwise mapping genes.

10 Claims, 2 Drawing Sheets

NUMBER OF GRAINS

DNA PROBE WHICH REVEALS A HYPERVARIABLE REGION ON HUMAN CHROMOSOME 17

This invention was made with government support under research which was funded in part by grant RO1-GM 32500 from the National Institutes of Health. The government has certain rights in the invention.

CROSS REFERENCE TO RELATED APPLICATION

This is a continuation-in-part of copending U.S. patent applications Ser. No. 046,831, filed May 4, 1987, and now abandoned, entitled "A DNA PROBE WHICH REVEALS A HYPERVARIABLE REGION ON HUMAN CHROMOSOME 1"; Ser. No. 053,320, filed May 22, 1987, entitled "A DNA PROBE WHICH REVEALS A HYPERVARIABLE REGION ON HUMAN CHROMOSOME 19"; Ser. No. 054,760, filed May, 27, 1987, which issued as U.S. Pat. No. 4,980,461 entitled "A DNA PROBE WHICH REVEALS A HYPERVARIABLE REGION ON HUMAN CHROMOSOME 2"; and Ser. No. 103,021, filed Sept. 30, 1987, which issued as U.S. Pat. No. 5,026,837 entitled "A DNA PROBE WHICH REVEALS A HYPERVARIABLE REGION ON HUMAN CHROMOSOME 16."

BACKGROUND OF THE INVENTION

1. Field of the Invention

The present invention concerns a restriction-enzyme-mapping probe for human chromosome 17.

2. General Discussion of the Background

Restriction fragment length polymorphisms (RFLPs) are different among individuals in the lengths of particular restriction fragments, Botstein, et al., *Am. J. Hum. Genet.*, 32:314-331 (1980). As the number of known RFLPs increases, they are becoming ever more useful in the prenatal or early diagnosis of numerous hereditary diseases. RFLPs are also used in mapping a diseased gene to a specific chromosomal location, which may serve as the first step in cloning the gene.

Diseases that have been mapped by linkage studies with RFLPs include Huntington's Disease, Gusella, et al., *Nature*, 306:234-238 (1983); Duchenne's muscular dystrophy, Murray, et al., *Nature*, 542-544 (1982); X-Linked Retinitis Pigmentosa, Bhattacharya, *Nature*, 309:253-255 (1984); adult polycystic kidney disease, Reeders, et al., *Nature*, 317:542-544 (1985); and cystic fibrosis, Tsui, et al., *Science*, 230:1054-1056 (1985). RFLPs also have been crucial to the elucidation of mechanisms underlying hereditary cancer syndromes frequently associated with chromosome deletions such as retinoblastoma, Cavenee, *Nature*, 305:779-784 (1983), and Wilm's tumor, Koufos, et al., *Nature*, 309:170-172 (1984). In the future, RFLPs may be useful in characterizing the genetic contributions to susceptibility to common diseases which tend to cluster in families, such as colon cancer and schizophrenia, White, et al., *Nature*, 313:101-105 (1985). For example, U.S. Pat. No. 4,623,619 discloses a method of using a probe to determine the propensity of specific human individuals to develop atherosclerosis.

RFLPs can also provide individual-specific "fingerprints" of human DNA which can be used for such forensic purposes as identification of corpses, paternity testing, and identification of rapists. For example, Jeffreys, et al. disclosed in *Nature*, 316:76-79 (1985) that simple tandem-repetitive regions of DNA ("minisatellites") which are dispersed throughout the human genome frequently show substantial length polymorphism arising from unequal exchanges which alter the number of short tandem repeats in a minisatellite. The repeat elements in a subset of human minisatellites share a common 10-15 base-pair core sequence. A hybridization probe consisting of the core repeated in tandem can detect many highly polymorphic minisatellites simultaneously to provide a set of genetic markers of general use in human linkage analysis. Certain probes can detect sets of hypervariable minisatellites to produce somatically stable DNA "fingerprints" which are completely specific to an individual (or an identical twin) and can be applied directly to problems of human identification, including parenthood testing. Unfortunately, the Jeffreys, et al., probe detects repeated sequences that occur throughout the entire human genome, and gives rise to very complex electrophoresis patterns that are sometimes difficult to interpret.

Hypervariable DNA regions have been reported near the human insulin gene (Bell, et al., *Nature*, 295:31-35 (1982)), in the α-globin gene cluster (Higgs, et al., *Nucleic Acids Res.*, 9:4213-4224 (1981); Proudfoot, et al., *Cell*, 31:553-563 (1982); Goodbourn, et al., *Proc. Natl. Acad. Sci. USA*, 80:5022-5026 (1983)), near the c-Ha-Ras-1 oncogene (Capon, et al., *Nature*, 302:33-37 (1983)) and at the telomere of the X and Y chromosomes (Cook, et al., *Nature*, 317:687-692 (1985)). In all cases where DNA sequence information in these regions is available, it shows that the region consists of tandemly repeated sequences which vary in copy number among chromosomes. These hypervariable regions are hypothesized to arise by mitotic or meiotic unequal crossing over or by DNA slippage during replication (Jeffreys, et al., (1985)). Hypervariable regions give rise to highly polymorphic loci at numerous genomic sites. DNA probes from such regions have been useful in paternity testing and other forensic applications as well as in human gene mapping.

It is therefore a primary object of this invention to provide a DNA probe which detects a hypervariable region of a human chromosome.

Another primary object is to provide such a probe which is specific to a single human chromosome.

Yet another primary object is to provide a probe which is easy to use and gives consistent results in forensic and medical tests.

SUMMARY OF THE INVENTION

The present invention includes a DNA probe, which is substantially homologous to at least a portion of a hypervariable DNA region located on the distal half of the short arm of human chromosome 17 (17p13). The DNA region displays a restriction fragment length polymorphism in humans when digested with certain restriction endonucleases.

In the disclosed embodiment, the probe is p144-D6. When used to probe Southern blots of RsaI-digested DNA's from 18 unrelated Northern European Caucasians, p144-D6 detected fourteen allelic fragments ranging in size from 1.65 to 5.3 kilobases (kb). The same locus was detected with several other enzymes, including TaqI and PstI.

A major advantage of p144-D6 is that it has at least fourteen allelic fragments and a polymorphism information content (PIC) of 0.86. The probe is a 5500 base-pair (bp) segment of human chromosome 17 cloned into the BamHI site of the vector pSP65. Preferably, the probe is radioactively labeled with $^{32}P$ and, in use, is hybridized with a Southern blot made from TaqI- or RsaI-digested human DNAs.

Broadly defined, the invention includes a recombinant DNA molecule containing a sequence substantially identical or homologous to at least a portion of the inserted sequence of probe p144-D6, the sequence being flanked by DNA segments that are not substantially the same as the DNA that flanks the inserted sequence in human chromosome 17. The recombinant DNA molecule consists of segments of DNA from different genomes which have been joined end-to-end outside of living cells. The invention also includes a vector containing a heterologous DNA sequence which is substantially identical or homologous to at least a portion of p144-D6.

The present invention includes a method of producing a distinctive genetic band pattern, or "fingerprint," from DNA isolated from a particular human individual. Whole human DNA is first digested with a restriction endonuclease. The resulting fragments are separated by agarose gel electrophoresis, partially transferred to a nitrocellulose filter, and probed with radiolabeled p144-D6. The labeled probe hybridizes to allelic fragments of DNA on the filter having sequences homologous to the probe. Autoradiographs of the filter reveal a distinct band pattern which can be used in human gene linkage analysis.

Probe p144-D6 hybridized to separated human DNA produces distinct band patterns which are characteristic of the individual person from which the DNA was taken. The band pattern can therefore be used for such forensic purposes as establishing the identity of a disfigured corpse or an accused assailant in a rape case. Medical applications include determining engraftment of bone marrow transplants, where it is helpful to determine if the marrow propagating in a patient's bone is diseased original tissue or healthy graft tissue. The probe can also be used to determine parentage because band patterns produced by the probes are inherited in a simple Mendelian fashion. Probe p144-D6 is also useful in chromosomal gene mapping because the probe is specific for a specific region on the distal half of the short arm of human chromosome 17 and can detect loss of chromosome 17 or a portion thereof during tumorigenesis.

A major advantage of p144-D6 over more highly polymorphic probes previously described is that the allelic fragments which it detects cover a broader size range and are therefore easier to resolve by agarose gel electrophoresis. The probe is therefore easy to use and gives consistent results.

The foregoing and other objects, features, and advantages of the invention will become more apparent from the following detailed description of a preferred embodiment which proceeds with reference to the accompanying drawings.

DETAILED DESCRIPTION OF PREFERRED EMBODIMENT

Figure 1:
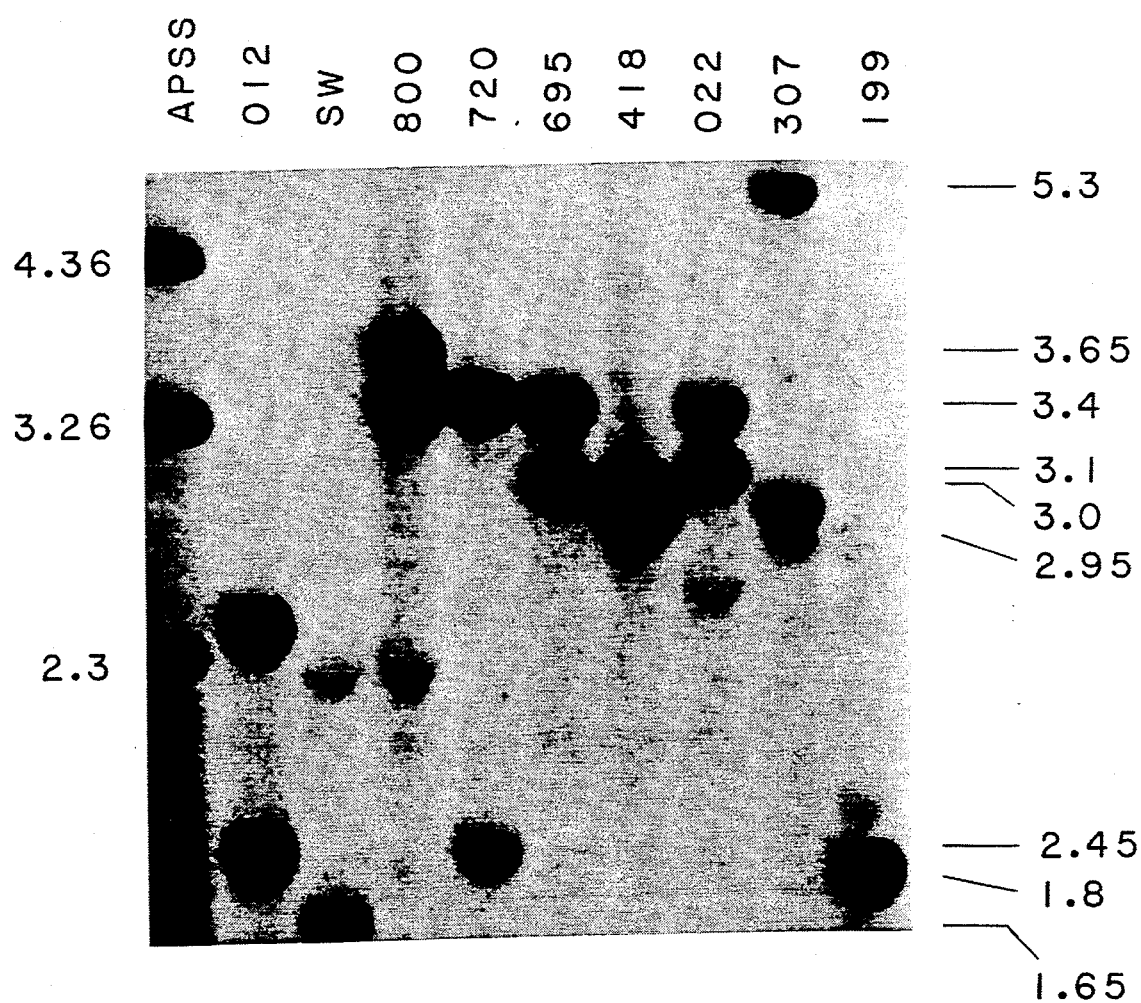
FIG. 1 is an autoradiograph of an RsaI blot of nine unrelated individuals probed with oligolabeled p144-D6. Lane 1 (labeled APSS) contains size standards.

For the construction of linkage maps of human chromosomes, marker loci with multiple alleles and a polymorphism information content (PIC) near 1.0 are very useful. Botstein, et al., *Am. J. Human Genet.*, 32:314–331 (1980). Although several hundred RFLPs have been reported to date, only about 10 percent have PIC values greater than 0.5. Willard, et al., *Cytogenet. Cell Genet.*, 40:360–490 (1985). The present inventors have addressed this problem of RFLP's having low PICs by using a method for rapidly screening cosmids and other repeat-containing DNA clones to identify those with inserts homologous to genomic regions especially rich in RFLPs. Litt and White, *Proc. Nat'l. Acad. Sci. USA*, 82:6206–6210 (1985).

Probe p144-D6 was isolated as a subclone from a human cosmid, c144. This cosmid was one of a collection of about 100 cosmids isolated from a chromosome 17-specific library constructed by Dr. Henrik Vissing and his colleagues. The construction and screening of this library is described in the article "Progress Towards Construction of a Total Restriction Fragment Map of a Human Chromosome" by Vissing, et al., *Nucleic Acids Research*, 15:1363–1375 (1987). Vissing provided a collection of cosmids for use as a source of probes to be screened to find several highly informative RFLPs.

Radioactively labled cosmid probes were prehybridized with a vast excess of nonradioactive total human DNA under conditions which drive repetitive (but not single copy) DNA into duplex form. These probes were used directly on Southern blots of restricted DNAs from panels of unrelated individuals to visualize low and single copy bands. Probes that displayed multiple polymorphisms by this method were further studied to obtain single copy subclones which revealed RFLPs. The inventors have successfully used these methods to characterize a highly polymorphic locus on chromosome 19 and isolate probe p13-1-25 which is homologous to that region. A detailed description of these methods can be found in Litt and White, *Proc. Nat. Acad. Sci. USA*, 82:6206–6210 (1985); Bufton, et al., *Am. J. Human Genet.*, 38:447–460; Bufton, et al., Hum. Genet., 74:425–431 (1986); Buroker, et al., *Hum. Genet.*, 72:86–94 (1986); Litt, et al., *Hum. Genet.*, 73:340–345 (1986).

Subclone p144-D6, which was isolated from cosmid c144 using these methods, reveals an insertion/deletion polymorphism. The designation D17S34 has been assigned to this locus by the Committee on Human Gene Mapping by Recombinant DNA Techniques.

METHODS OF PREPARING COSMID AND SUBCLONES

Human DNA isolation from white blood cells (WBC), cosmid preparation and screening, subcloning, restriction mapping and hybridization procedures, and in situ hybridization methods have been described in Litt and White (1985); Bufton, et al. (1986); Buroker, et al. (1986); and Litt, et al. (1986). Southern blots used in this study were hybridized at 45°–57° C. and given a final wash in 0.1XSSC, 0.1-percent SDS at 65° C. DNAs from 3-generation Utah familes were extracted from lymphoblast cell lines obtained from the Institute for Medical Research, Camden, N.J.

Cosmids revealing possible polymorphisms were subcloned into the plasmid pSP65 (Promega Biotec, Madison, Wis.), a 3 kb ampicillin-resistant plasmid with a polylinker containing 11 unique restriction sites for cloning. Cosmid DNA was digested with Sau3A, phenol/chloroform extracted, ethanol precipitated, dissolved in TE$^{-4}$, and ligated into the BamHI site of BamHI-cut and phosphatased pSP65 using 100 ng of insert DNA per microgram of vector DNA with reagents and conditions as previously described. Competent E. coli HB101 bacteria were transformed with the recombinant plasmids using standard techniques (Maniatis, et al. (1982)) and transformed colonies selected on ampicillin plates. The clones were screened by colony hybridization using oligolabeled total human DNA and appropriate oligolabeled restriction fragments from the cosmid. DNA was isolated from the subclones of interest by the Birnboim alkaline miniprep method (Birnboim (1983)).

Southern Blotting and Hybridization

Source and Preparation of Human DNA

Human DNAs were prepared from outdated whole human blood obtained from the local blood bank and from lymphoblast cell lines of large Utah families obtained from the Human Genetic Mutant Cell Repository, Institute for Medical Research, Camden, N.J., using the method of Kunkel (Bell, et al. (1981)) with the addition of a second ethanol precipitation in the presence of 2.5 M ammonium acetate. Restriction enzymes were obtained from Promega Biotec, New England Biolabs, Bethesda Research Labs, and Boehringer Mannheim, and used according to the manufacturers' instructions. Human DNAs were digested with 5-10 units of enzyme per microgram of DNA and completeness of digestion assessed by agarose gel electrophoresis of parallel digests containing λ DNA in addition to human DNA (Barker et al., Cell, 36:131-138 (1984a)). Complete digests were ethanol precipated and dissolved in TE.

Southern blotting

The digested total human DNAs were electrophoresed through agarose gels, transferred to nylon membranes (Gene Screen from New England Nuclear, Genatran from D and L Filter, Woburn, Mass., or Zetapore from AMF-CUNO, Meriden, Conn.), washed and prehybridized according to Barker, et al., Am. J. Hum. Genet., 36:1159-1171 (1984b).

Hybridization

Radiolabeled whole cosmids were screened on Southern blots for their utility in revealing RFLPs. They were nick-translated (Barker, et al. (1984a)) in the presence of α-$^{32}$P dATP to give specific activities of at least 2×10$^8$ dpm/µg. After removal of unincorporated radioactivity by spermine precipitation (Hoopes and McClure, Nucleic Acids Res., 9:5493-5504 (1981)), the cosmid probes were mixed with a vast excess (625 µg/100-200 ng cosmid DNA) of non-radioactive 2.5 mg/mL sonicated (500 bp) human placental DNA (Calbiochem, La Jolla, Calif.), heated at 100° C. for 10 minutes, and prehybridized to a c$_o$t of about 100 moles-sec/L by incubation in 0.12 M sodium phosphate, pH 7, at 65° C. for 4-6 hours (Litt and White, Proc. Nat'l Acad. Sci. USA, 82:6206-6210 (1985)).

These prehybridized probes were then hybridized with Southern blots of TaqI- and RsaI-digested genomic DNAs from a panel of unrelated individuals. Hybridization was overnight at 43°-45° C. in hybridization solution with dextran sulfate. The blots were then washed in 2X SSC/0.1-percent SDS at room temperature for 15 minutes, once in 0.1X SSC/0.1-percent SDS at room temperature for 15 minutes, and twice in 0.1X SSC/0.1-percent SDS at 65°-69° C. for 30 minutes. The blots were dried on paper towels, wrapped in Saran wrap, and exposed for 1 to 7 days to Kodak XAR-5 film backed by an intensifying screen at −70° C.

In Situ Hybridization

Probe p144D6 was nick-translated according to the method of Harper and Saunders, (Chromosoma, 83:431-439 (1981)) to a specific activity of 4×10$^7$ dpm/µg using [$^3$H]TTP (65 Ci/mmol) and [$^3$H]dClP (60 Ci/mmol)(Amersham). In situ hybridization to metaphase spreads from normal male cells was performed according to Harper and Saunders (1981).

Results

Cosmid c144 was labeled by nick translation, prehybridized with total human DNA and screened on Southern blots containing TaqI- and RsaI-digested DNA from six to nine unrelated individuals. The autoradiographs of these blots showed multiple allele RFLPs with both enzymes. However, the quality of these autoradiographs was not consistently good and the yields of c144 were low. Therefore, a small segment of c144 was isolated by subcloning that could be used as a probe to detect the RFLP but which might give cleaner, more consistent autoradiographs and which should be much easier than the cosmid to isolate in high yield.

Sau3A fragments of c144 were subcloned into the BamH1 site of the plasmid vector pSP65. Subclones were screened for presence of repeated sequences by hybridization with total human DNA; those that failed to hybridize were likely to be single-copy in the human genome and hence were useful candidates for probes to reveal the multiple allele RFLP seen with the whole cosmid.

Subclone p144-D6 amply fulfilled these expectations. This subclone, with a 5.5 kb Sau3A insert, revealed an RsaI polymorphism with 14 alleles detected in nine unreleated individuals, ranging in size between 1.65 and 5.3 kb. On short autoradiographic exposures, these allelic fragments were the only ones detected. However, after prolonged exposures, such as that shown in FIG. 1, a faint constant band with size <1 kb and one to four additional faint variable bands were detected. These results indicate that p144-D6 hybridizes weakly to at least one additional locus in the human genome. Because the faint bands were difficult to detect reproducibly, and because they could readily be eliminated by limiting the autoradiographic exposure, further studies were entirely confined to the strong bands that represent hybridization of p144-D6 to the major locus. The alleles at this locus and their frequencies are shown in Table 1.

TABLE 1

| | p144-D6 RFLP |
|---|---|
| Allele (kb) | Frequency (18 chromosomes) |
| 5.30 | .083 |
| 3.80 | .028 |
| 3.50 | .167 |
| 3.40 | .028 |

TABLE 1-continued

| p144-D6 RFLP | |
|---|---|
| Allele (kb) | Frequency (18 chromosomes) |
| 3.30 | .028 |
| 3.20 | .055 |
| 3.10 | .167 |
| 3.05 | .055 |
| 3.00 | .055 |
| 2.80 | .028 |
| 2.55 | .028 |
| 2.50 | .028 |
| 1.85 | .220 |
| 1.65 | .028 |

A similar RFLP was seen with TaqI, MspI and PstI, but fragment sizes and allele frequencies seen with these enzymes were not investigated further.

The RFLP was studied in three 3-generation families with a total of 38 children and codominant Mendelian inheritance was observed in all cases.

Because the origin of p144-D6 was from a chromosome 17-specific library, it was expected that the RFLP revealed by this probe would be on chromosome 17. This was confirmed, and regional localization obtained, by in situ hybridization.

Figure 2:
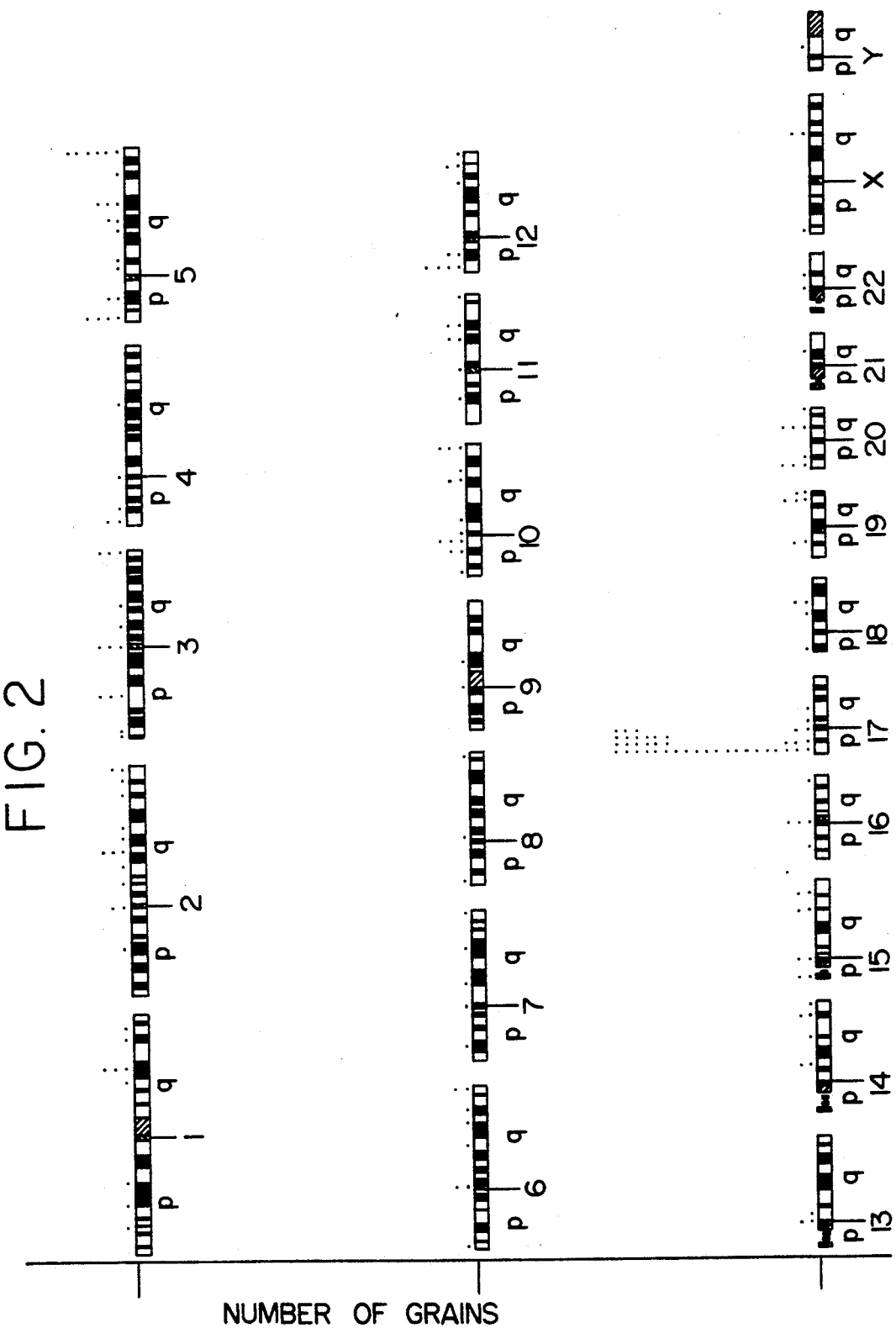
FIG. 2 is a histogram of chromosomal distribution of silver grains from in situ hybridization of p144-D6 to chromosomes of a normal male.

FIG. 2 summarizes the results of scoring 110 labeled metaphase spreads from a normal male. Thirty-five of the 110 metaphases (32 percent) showed hybridization to the distal portion of 17p (17p13); the rest of the label was randomly distributed over the chromosomes.

The name D17S34 has been assigned to the locus which maps to 17p13, has at least 14 alleles, and has a PIC of 0.86. Subclone p144-D6 detects this locus.

Substantially Homologous Probes

The present invention includes DNA probes which contain a sequence substantially homologous or substantially identical to at least a portion of the base pair sequence of probe p144-D6. A substantially homologous sequence is one in which a high degree of homology between the sequences of two or more DNA molecules can be tested for by determining whether the DNA molecules in question hybridize to each other under stringent conditions, such as those set forth in Bethesda Research Laboratories, *DNA Detection System Instruction Manual* (Catalogue No. 8239SA), pp. 8–9 (1984). *See also* Leary, et al., *Proc. Natl. Acad. Sci. USA*, 80:4045–4049 (1983), modifying the procedures of Wahl, et al., *Proc. Natl. Acad. Sci. USA*, 76:3683–3687 (1979).

Probe Uses

The DNA fingerprints produced by probe p144-D6 are sufficiently stable and individual-specific for use in human identification in, for example, forensic medicine. Badly disfigured corpses can be identified by preparing a genetic fingerprint with probe p144-D6, and comparing the fingerprint to bands produced by DNA of a previously collected tissue sample from a known individual who is believed to be the corpse. If the band patterns match, identity has probably been established. Rapists can similarly be identified by comparing the band patterns from semen in the victim with the band patterns produced by the DNA of an individual suspected of committing the crime.

The simple Mendelian inheritance of band patterns produced by p144-D6 makes it possible to use the probe in determining parentage, for example, in a disputed paternity suit. Approximately half of the polymorphic fragments in an offspring are derived from the father, and these paternal fragments can be identified by comparison of the mother's and offspring's DNA band patterns. All fragments present in the offspring but not in the mother must be present in the father (allowing for a possible rare new mutation). The large number of polymorphic fragments makes it possible not only to exclude paternity, if bands are present in the offspring but not the mother or putative father, but also to predict statistically the possibility of inclusion of paternity.

Probe p144-D6 is a potentially useful tool for following engraftment of donor bone marrow after transplantation (Blazar, et al., *Blood*, 66:1436–1444 (1985)), and for many forensic applications. Furthermore, p144-D6 might be useful in isolating genomic clones capable of revealing additional hypervariable regions.

RFLPs are also useful in cancer research to determine clonal origin of tumors and to study the loss of heterozygosity at various gene loci. Vogelstein, et al., *Science*, 227:642–644 (1985); Dracopoli, et al., *Proc. Natl. Acad. Sci. USA*, 82:1470–1474 (1985).

Restriction Enzyme Mapping

Probe p144-D6 can also be used to map genes on chromosomes using the techniques disclosed by Gusella, et al. (1983), Murray, et al. (1982), Bhattacharya, et al. (1984), Reeders, et al. (1985) or Tsui, et al. (1985). A disease gene can be located by using the knowledge that a RFLP closely linked to a gene would be inherited with that gene. The inheritance of numerous RFLPs in families having the disease can be traced using random cloned DNA fragments from a human gene library as probes. An RFLP which is found to be inherited along with the disease indicates that the RFLP and disease gene are closely linked. Probe p144-D6 will therefore indicate the presence of a disease gene on the short arm of human chromosome 17.

ATCC Deposit

Probe p144-D6 has been deposited with American Type Culture Collection in Rockville, Md., and assigned ATCC accession No. 67678. The deposited probe is a plasmid containing an insert DNA from cosmid c144. In use, the probe would be amplified through bacterial transformation to produce a bacterial colony. The plasmid would then be isolated and labeled, for example, with radioactive phosphorous.

Having illustrated and described the principles of the invention in a preferred embodiment, it should be apparent to those skilled in the art that the invention can be modified in arrangement and detail without departing from such principles. We claim all modifications coming within the spirit and scope of the following claims.

We claim:

1. A plasmid having ATCC accession No. 67678 which contains a clone of DNA probe p144-D6.

2. A DNA probe containing a sequence consisting of the inserted DNA of a plasmid having ATCC accession No. 67678, which insert hybridizes to locus D17S34 of the human genome.

3. The probe of claim 2 further comprising a label which enables detection of the probe.

4. A recombinant DNA molecule consisting essentially of:

A DNA segment consisting essentially of the base sequence of probe p144-D6; and a label for detecting the sequence.

5. The molecule of claim 4 that is a plasmid.

6. The probe of claim 4 wherein the label is a radioactive material.

7. A DNA probe consisting essentially of the DNA sequence of p144-D6.

8. A DNA probe having a nucleotide sequence which hybridizes to a hypervariable region of the human genome at locus D17S34 of chromosome 17 and reveals a multiple allele RFLP with at least 14 fragments varying in size from 1.65 to 5.3 kb when used to probe Southern blots of RsaI-digested DNA, wherein the nucleotide sequence is identical to at least a portion of locus D17S34.

9. The probe of claim 3 wherein the label is a radioactive material.

10. The probe of claim 9 wherein the radioactive material is phosphorus.

* * * * *

UNITED STATES PATENT AND TRADEMARK OFFICE
CERTIFICATE OF CORRECTION

PATENT NO. : 5,077,400

DATED : December 31, 1991

INVENTOR(S) : Michael Litt and Sophia K. Kondoleon

It is certified that error appears in the above-identified patent and that said Letters Patent is hereby corrected as shown below:

Column 1, line 21 reads, "May, 27, 1987," and should read --May 27, 1987--.

Column 1, line 47 reads, "Nature, 542-544" and should read --Nature, 300:542-544--.

Column 8, line 34 reads, "library. as probes." and should read --library as probes--.

Column 6, line 13 reads, "p144D6" and should read --p144-D6--.

Column 8, line 59 reads, "sequence consisting of" and should read --sequence consisting essentially of--.

Signed and Sealed this

Eighth Day of June, 1993

Attest:

MICHAEL K. KIRK

*Attesting Officer*     *Acting Commissioner of Patents and Trademarks*